(12) United States Patent
Filsoof

(10) Patent No.: US 11,672,687 B1
(45) Date of Patent: Jun. 13, 2023

(54) APPARATUS FOR NECK SUPPORT

(71) Applicant: Mahmud Filsoof, Pacific Palasade, CA (US)

(72) Inventor: Mahmud Filsoof, Pacific Palasade, CA (US)

( * ) Notice: Subject to any disclaimer, the term of this patent is extended or adjusted under 35 U.S.C. 154(b) by 0 days.

(21) Appl. No.: 17/840,645

(22) Filed: Jun. 15, 2022

Related U.S. Application Data

(60) Provisional application No. 63/334,200, filed on Apr. 25, 2022.

(51) Int. Cl.
*A61F 5/05* (2006.01)
*A61F 5/055* (2006.01)
*A61F 5/058* (2006.01)

(52) U.S. Cl.
CPC .......... *A61F 5/055* (2013.01); *A61F 5/05883* (2013.01)

(58) Field of Classification Search
CPC ... A61F 5/055; A61F 5/05883; A61F 5/05808
See application file for complete search history.

(56) References Cited

U.S. PATENT DOCUMENTS

| | | | | |
|---|---|---|---|---|
| 2,807,260 A * | 9/1957 | Teufel | ...................... | A61F 5/055 602/17 |
| 2,820,455 A * | 1/1958 | Hall | ........................ | A61F 5/055 602/18 |
| 3,177,869 A * | 4/1965 | Bartels | ..................... | A61F 5/055 602/18 |
| 3,776,224 A * | 12/1973 | McFarland | ............. | A61F 5/055 602/18 |
| 5,840,051 A * | 11/1998 | Towsley | ................ | A61F 5/0125 602/19 |
| 6,267,741 B1 * | 7/2001 | Lerman | ................... | A61F 5/055 602/18 |
| 8,057,415 B2 * | 11/2011 | Hipp | ....................... | A61F 5/055 602/18 |
| 9,949,758 B2 * | 4/2018 | Vikinsky | ................ | A61B 90/06 |
| 11,291,575 B2 * | 4/2022 | Briant | ........................ | A61F 5/01 |
| 2008/0156332 A1 * | 7/2008 | Ray | .......................... | A61F 5/055 128/845 |
| 2014/0081180 A1 * | 3/2014 | Ghajar | .................... | A61F 5/055 600/595 |
| 2014/0228728 A1 * | 8/2014 | Bonutti | ..................... | A61F 5/02 602/19 |
| 2015/0133840 A1 * | 5/2015 | Calabrese | ............... | A61F 5/055 602/18 |

(Continued)

*Primary Examiner* — LaToya M Louis
(74) *Attorney, Agent, or Firm* — Alexander Chen, Esq.

(57) ABSTRACT

An improved head/neck support device has a disc base that is attached to a hollow tube that in turn receives a first cylindrical component that has a sleeve attached to its outside wall. The device further has a spring coil disposed in the gap between the first cylindrical component and a second cylindrical component, that has a lower portion that has a diameter equal to the spring coil's and a smaller diameter upper portion. The device also has a second hollow tube that engages with the second cylindrical component and constrains the second cylindrical component from sliding out and through the second tube. The device also has a horseshoe shaped elastic band attached to the outer wall of the second tube. The device further has a chin rest that has a third hollow tube, a disc, and a top pad.

6 Claims, 11 Drawing Sheets

(56) References Cited

U.S. PATENT DOCUMENTS

| | | | |
|---|---|---|---|
| 2015/0245940 A1* | 9/2015 | Hardcastle | A63B 21/4025 |
| | | | 602/18 |
| 2015/0305913 A1* | 10/2015 | Calegory | A61F 5/055 |
| | | | 602/17 |
| 2017/0202638 A1* | 7/2017 | Schiffman | A61G 15/125 |
| 2018/0360642 A1* | 12/2018 | Izquierdo Gadea | A61F 5/055 |
| 2020/0390582 A1* | 12/2020 | Filsoof | A61F 5/05883 |
| 2021/0330486 A1* | 10/2021 | Kuang | A61F 5/56 |

* cited by examiner

--Prior Art--

--Prior Art--

--Prior Art--

--Prior Art--

--Prior Art--

--Prior Art--

--Prior Art--

APPARATUS FOR NECK SUPPORT

INCORPORATED BY REFERENCE

This application claims the benefit of priority to the filing date of U.S. Provisional application No. 63/334,200, entitled "Neck Support Device," which was filed on Apr. 25, 2022, and which are incorporated herein by reference in its entirety.

FIELD OF INVENTION

The present invention is directed generally to a system and apparatus for neck therapy that addresses the need for ventilation. Specifically, it is directed to a system and apparatus of a neck support for medical purposes that reduces the potential for moisture accumulation on the user's skin as compared to traditional neck support apparatuses.

BACKGROUND OF THE INVENTION

Neck braces or cervical collars are commonly used within the medical and therapeutic communities to support a patient's neck whose muscle, cervical vertebrae, or discs have received trauma. Because of the critical nerves involved in the neck, and the fact that an adult's head generally weighs around 10 lbs which is entirely supported by the neck when the neck is weakened, it is important to support and stabilize the mass of the patient's head in order to avoid further injuries and complications. The braces and collars generally immobilize the wearer's head while relieving the pressure on the spine by structurally supporting the weight of the head against the patient's upper chest, shoulders, and clavicle region.

The purpose of a collar is to support the spinal column and supporting structures such as the ligaments and muscles from loads and stresses that can cause pain and movement of the neck bones. It also maintains the bone alignment and limits the movement in your neck whilst the bones and ligaments heal.

There are many neck braces, or, in general, neck support devices, in the market. Most of them is made of foam and bulky. They wrap around, and completely surround the user's neck. These neck braces are difficult to ventilate, wearing a brace will increase your body temperature in that region, causing moisture to accumulate, and, as a consequence, the user's neck becomes sweaty and irritated from the accumulated sweat. While sometimes it may simply be a matter of adjusting or refitting the collar.

This discomfort is exacerbated during summer months or in tropical or warmer climates. This discomfort potentially may interfere with the neck therapy the user is receiving. Ultimately, the fault of these neck braces is that they rest the weight of the user's head, neck and the braces on the base of the neck and/or the shoulders. Thus, they wrap around a user's neck and must be somewhat rigid and solid. Thus, most of the current neck braces on the market don't ventilate very well.

Because the brace is itchy, uncomfortable and sweaty conditions, many users don't use them according to the directions given to them by their healthcare providers, removing them when they shouldn't, or poke and prod around the braces attempting to relieve discomfort.

Obviously, this is counterproductive and may by itself cause health problems or at minimum, exacerbate the patient's original injuries that the neck brace is meant to treat.

What is frustrating however is that as to the current state of the art, when a patient perseveres this discomfort and does use the neck brace according to a healthcare providers direction it is known that the cervical collars seen in the marketplace can cause pressure sores or ulcers.

Pressure injuries can be difficult to treat and can lead to serious complications. Pressure sores (more recently called pressure injuries) are areas of damage to the skin and underlying tissue caused by constant pressure or friction. By wearing a collar, a patient increases the local skin temperature between the device and their skin, thus naturally causing skin perspiration in and around the area. This moisture can exasperate the issue and cause skin breakdown.

Pressure sores are graded to four levels, including:

grade I—skin discolouration, usually red, blue, purple or black This is the mildest stage. These pressure sores only affect the upper layer of your skin.

Symptoms: Pain, burning, or itching are common symptoms. The spot may also feel different from the surrounding skin: firmer or softer, warmer or cooler.

grade II—some skin loss or damage involving the topmost skin layers. This happens when the sore digs deeper below the surface of your skin.

Symptoms: The skin is broken, leaves an open wound, or looks like a pus-filled blister. The area is swollen, warm, and/or red. The sore may ooze clear fluid or pus. And it's painful.

grade III—necrosis (death) or damage to the skin patch, limited to the skin layers.

grade IV—necrosis (death) or damage to the skin patch and underlying structures, such as tendon, joint or bone.

Both simple grade 1 pressure ulcers (redness, intact skin) and grade 2 ulcers (partial thickness loss of skin, shallow open blister) can be self-managed by applying a skin protector or dressing. Further grades of pressure ulcers require contacting the neurosurgical team as more complicated intervention is required.

In patients with moist skin, skin breakdown is increased fourfold, compared to those with dry skin.

Also, when a patient doesn't clean their brace regularly, they not only start to smell bad, but they also can sometimes cause health problems, such as folliculitis, ringworm and even staph infections.

To alleviate and prevent these issues, healthcare providers recommended that a patient take the following precautions: (1) Keep the skin clean, dry and cool; (2) Maintain hygiene under the collar, cleaning the skin under the collar daily; washing with warm soapy water and drying thoroughly; and (3) Changing pads on the neck brace/collar if they become wet.

While these recommendations seem fairly innocuous, as discussed, neck injuries are particularly serious and the potential for needless risk must be considered.

Accordingly, it is desirable to have a neck brace or neck support device that provides adequate support to the neck while allowing air circulation and ventilation, such that a user or patient is not required to remove the brace in order to dry and clean the neck and brace.

Further, as discussed, the current state of the art devices most often wrap around a user's neck and are rigid and solid in nature. Because of this, the devices are most often made by injection molding solid plastic pieces. As a consequence, and in order to bring down production costs, the devices currently seen in the market, are fairly limited when it comes to sizes and adjusting the fit of these devices.

Most commonly, current devices are manufactured in a gross range of small, medium, and large size variability, with the ability to tighten and somewhat customize the snugness limited to the number of adjustment points that can be molded into the plastic, similar to the size adjustment that one might expect with a snapback baseball cap, or ski bindings, and the like. Alternatively, with the foam variants of neck braces, in lieu of a rigid adjustment lock-in point, those devices often employ Velcro. While Velcro does allow for a more custom fit, anyone familiar with Velcro will readily recall that it often loses its grip such that a tight fit is difficult to maintain. Additionally, the foam used in these braces, much like with foam mattresses, retain heat, and exasperate the above describes moisture issues.

As such, it is additionally desirable to have a neck brace or neck support device that provides adequate support to the neck while allowing for customization of fitting on a micro incremental scale, a better fit granting better overall comfort, and likely leading to better healing and a higher quality of life for a user when using the device for prolonged periods as are often required with such injuries.

Previous neck brace or neck support device devised by the applicant was cumbersome to produce and this improved version extensively reduced the moving parts and cost of production.

SUMMARY OF THE INVENTION

A head and/or neck support device comprising a base component comprising a disc that further comprises a top portion and a bottom portion; wherein the bottom portion is a bottom pad that is attached to and removable from the top portion; wherein the top portion is attached to a hollow tube at its slanted end; wherein the base disc is disposed on to the slanted end and thereby rest on a downward slope of a user's sternum; wherein when the base component sits on the sternum, allowing the head and/or neck support device to provide support for the chin of the user; wherein the hollow tube further comprises two vertical grooves on the inside walls of the tube and opposite to each other; a first cylindrical component that has a smaller diameter than that of the hollow tube so that the cylindrical component can be inserted therein; wherein the outer wall of the first cylindrical component are disposed of two vertical ridges opposite each other and made to mate with the vertical grooves; wherein a sleeve attached to the outside wall wherein the sleeve has a larger diameter which is at least equal to that of the first cylinder component; wherein the sleeve is disposed about the middle of the cylindrical component; wherein two tabs disposed on the outer wall about the edge thereof, and opposite each other thereby allowing a gap between the tabs and the sleeve; wherein the lower half of the first cylindrical component is inserted into the hollow tube of the base component while the portion above the sleeve extends up to support other components of the device; a spring coil that has a diameter larger than that of the first cylindrical component, but smaller than that of the sleeve and is disposed in the gap between the first cylindrical component and a second cylindrical component wherein the tabs holds the first cylindrical component securely with a second hollow tube; the second cylindrical component comprising a lower portion that has a diameter equal to that of the spring coil, such that the cylindrical component cannot be deposited inside the spring coil; wherein an upper portion that has a smaller diameter than the lower portion wherein the upper portion further comprises two vertical ridges disposed on its outer wall and opposite each other; the second hollow tube further comprises two vertical grooves, opposite each other and on the inner wall thereof; wherein the grooves engages with the ridges of the upper portion of the second cylindrical component such that the ridges slide and sit in on the grooves wherein the ridges constrains the tube from rotating relative to the second cylindrical components, and the device; a horseshoe shaped elastic band attached to the outer wall of the second hollow tube wherein the elasticity of the band allows the gap between the band's left and right parts to open wider so the user could put the band on and around the user's neck; a chin rest comprises a hollow tube, a disc, and a top pad wherein the disc is attached to the slanted end of the tube wherein the top disc is disposed slanted toward the user, and allows the user's chin rests comfortably on it. In one embodiment, the bottom pad that is attached to and removable from the top portion via a Velcro patch. In another embodiment, the bottom pad is made of elastic materials. In another embodiment, the elastic materials is a memory foam. In another embodiment, the top pad is attached to and removable from the top disc. In another embodiment, the top pad further provides comfort to the user with its conforming material.

DETAILED DESCRIPTION OF THE CURRENT INVENTION

Figure 1:
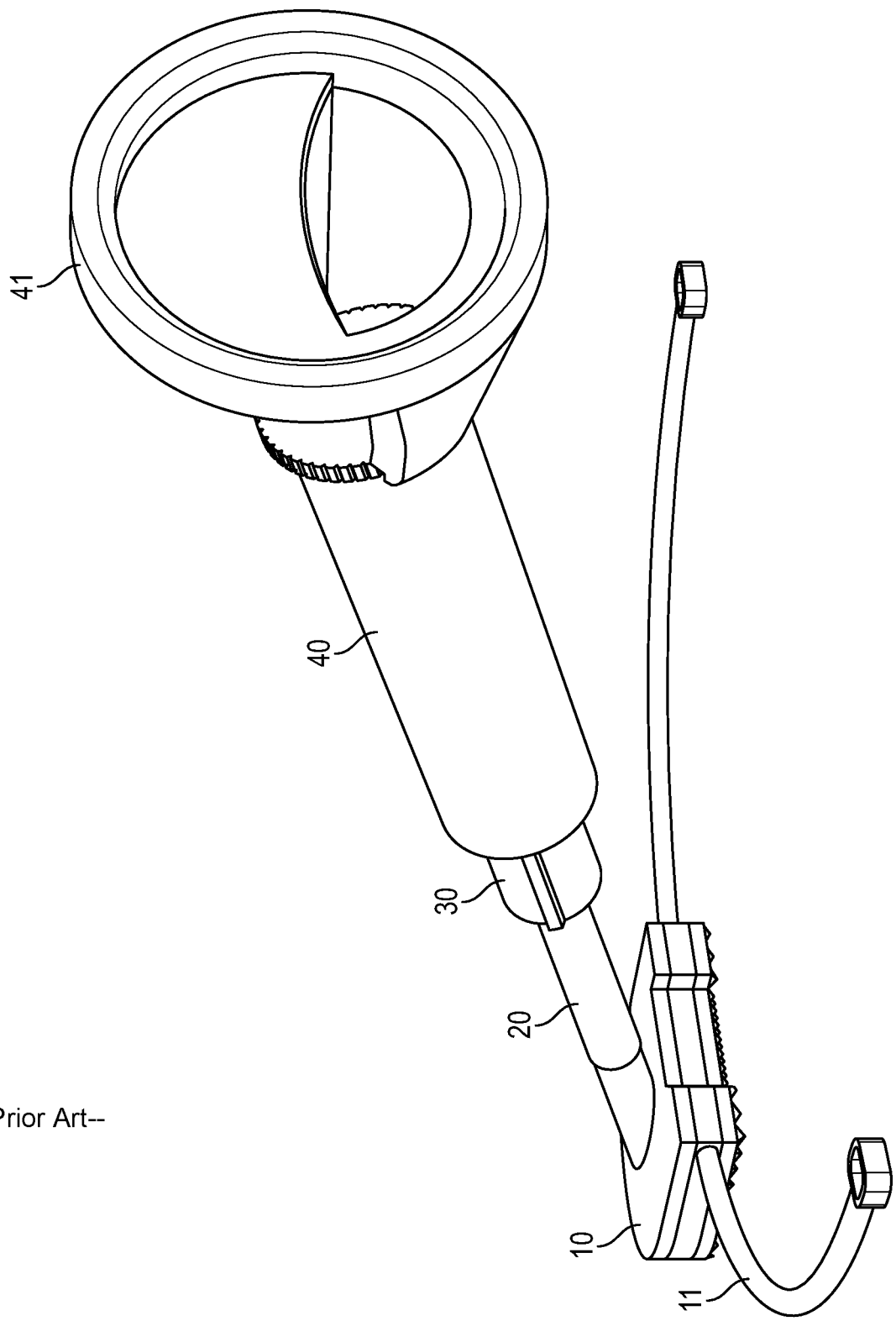
FIG. 1 illustrates a fully assembled embodiment of the prior invention.

In FIG. 1, a fully assembled embodiment 1 of the prior invention is depicted. This embodiment 1 comprises a base component 10 that, when in use, rests on the user/patient's sternum and supports the weight pushing down on the device. The base component 10 further comprises a belt 11 that is attached to the base and extends and wraps around the user/patient's body to the back, and its two ends hook on each other. The embodiment 1 further comprises a cylinder 20 that is inserted into the cylinder slot on the base 10. The cylinder 20 extends upward and screws into a cylinder 30. This cylinder 30 is, in turn, partially disposed inside the hollow cylinder of a component 40 that comprises the hollow cylinder and a chin rest 41 that is molded onto the outer side of the hollow cylinder.

Figure 2:
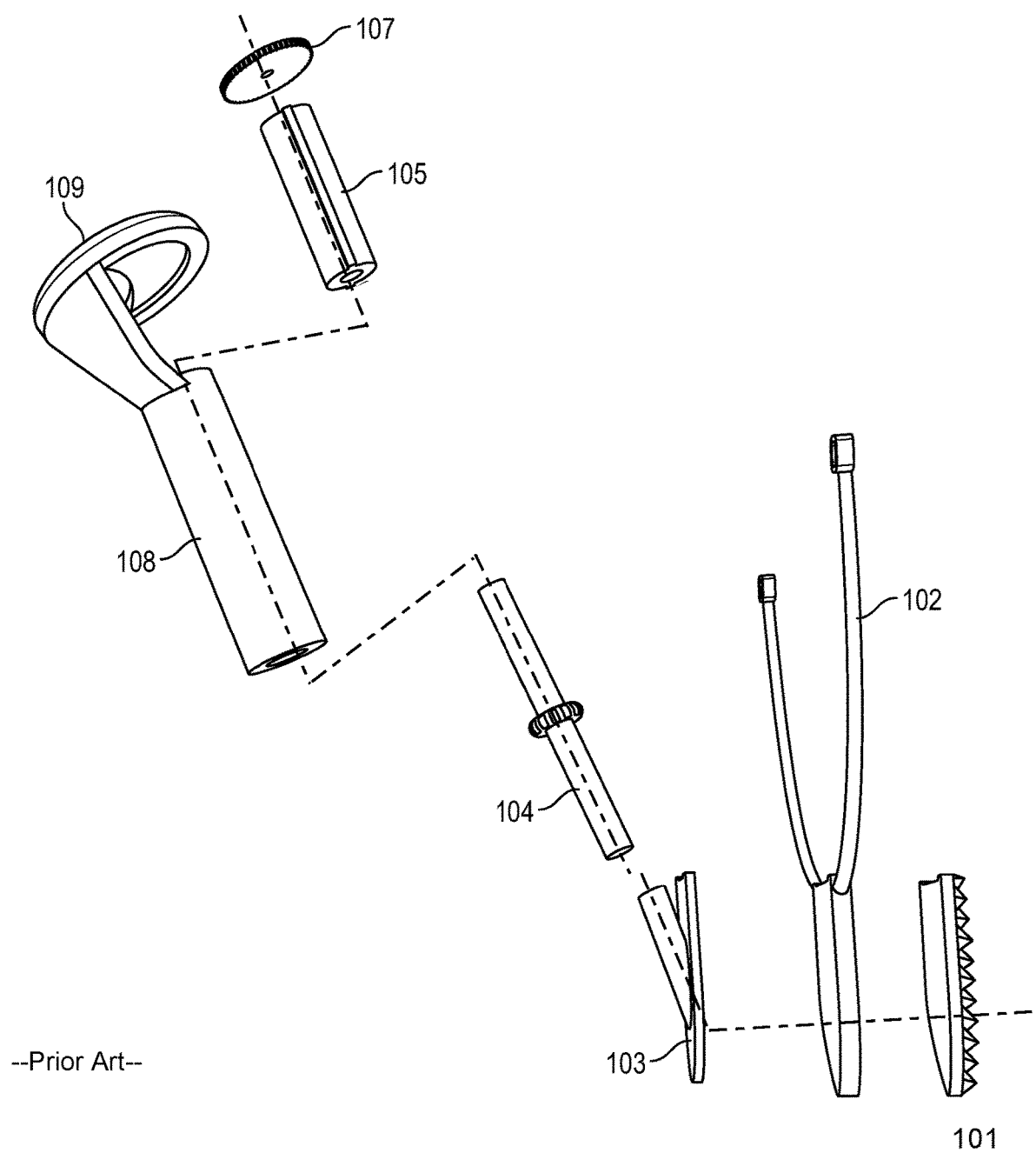
FIG. 2 is a pictorial illustration of an exploded view of the prior invention meant to communicate the various individually machine produced components, their approximate location to other components in the final assembly, and a suggestion of materials making up those components.

Reference is now made to FIG. 2, a pictorial illustration of an exploded view of the prior invention meant to communicate the various individually machine produced components, their approximate location to other components in the final assembly, and a suggestion of materials making up those components, constructed and operative in accordance with an embodiment of the present invention.

As with neck braces that are currently common, a majority of the components in the preferred embodiment of the invention at issue are either injected molded plastics and or some other combination of light weight cost effective metals and alloys in order to keep both the cost of the device itself practical, but balanced against the need for lightweight but sufficiently strong materials that can be expected to support the weight of the users head for the purposes of the device while keeping the cumulative weight of the device light and comfortable for the user such that it is easy to wear for the extended period of time that the invention is expected to be used.

In FIG. 2, an embodiment of the prior invention in one part comprises three large horizontally bisected flattened capsule-shaped plates that stack to create the support base of the device, similar to the support base 10 disclosed supra in FIG. 1. Component 103 is a thick hard rubberized material piece that is designed with an incorporated angled subset cylinder which allows a cylindrical structure to be disposed within. Component 103 is, in turn, stacked on top of component 102, a similar bisected flattened capsule plate which will provide support for the device and which incorporates the two curved attachment arms which each have a mechanical attachment point at their ends. An adjustable belt will connect to these arms of 102 that will wrap and follow around the user's back to provide support for the device. Component 102 is, in turn, stacked on top of component 101, which is the innermost user facing layer of this 3 part support base and designed to have soft padding and to rest at the top of the user's sternum.

As was discussed previously, the design and mechanics of the prior invention is the emphasis of this patent. As such, it is contemplated that many of the materials used for the components of the invention would be the same or similar as many of the same materials used in the current state of the art. As such, it is anticipated that injected molded plastic processes, aluminum, stainless steel, titanium, and other light weight, cost effective, medically appropriate materials will be sourced as to the current invention.

In FIG. 2, the embodiment of the prior invention further comprises additional cylindrical components which comprise the mechanical support arm apparatus for the user's chin, neck and head. Cylinder 104 is disposed within the subset cylinder cavity of component 103 to provide support for cylinders 105 and 108. Cylinder 105 is female threaded to receive cylinder 104, which is male threaded. Both cylinders 104 and 105 are threaded with fine threads such that the height or length of this support arm can be extended and refined in micro increments and allow for very flexible adjustment and thus provide a more precise support for the neck as compared to traditional neck braces currently seen in practice. Cylinder 108 extends up and further comprises an incorporated soft chin support component 109 upon which the users rests their chin.

The embodiment further comprises a spring (not shown in FIG. 2) that is disposed within Cylinder 108's cavity and sandwiched and compressed between cylinder 105 and cylinder 108's cavity. The spring elasticity allows for limited and controlled neck movement, and softens the prodding force against the chin similar to shock absorbers seen in the automotive industry. For example, while the neck is tilted at a 15 degree angle the spring will assist in relieving pressure.

Cylinder 108 further comprises a locking mechanism that allows cylinder 105 and the spring to lock at a user's desired angle, similar to the locking mechanisms seen in retractable ballpoint ink pens. While locking the spring creates a static and rigid support, more traumatic and complicated neck injuries often initially require little to no movement early on in the recovery period. Furthermore, many patients experience fatigue over the course of the day, and it is desirable to incorporate this locking functionality such that the device can be fitted and turned to suit the needs of the patient.

Figure 3:
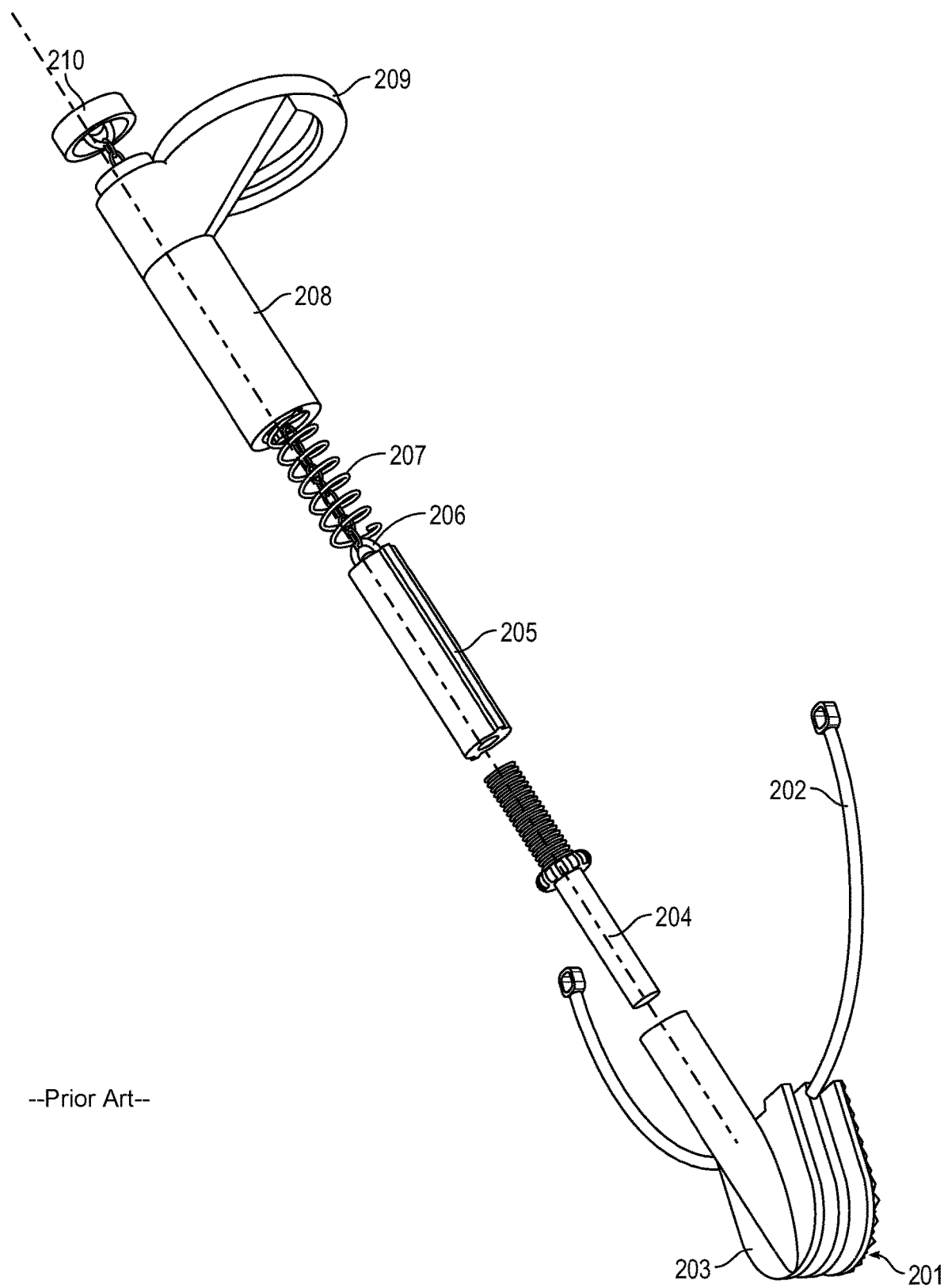
FIG. 3 is a pictorial illustration of an exploded side view of the prior invention, meant to communicate more specifically the assembly of the various individually machine produced components.
Figure 4:
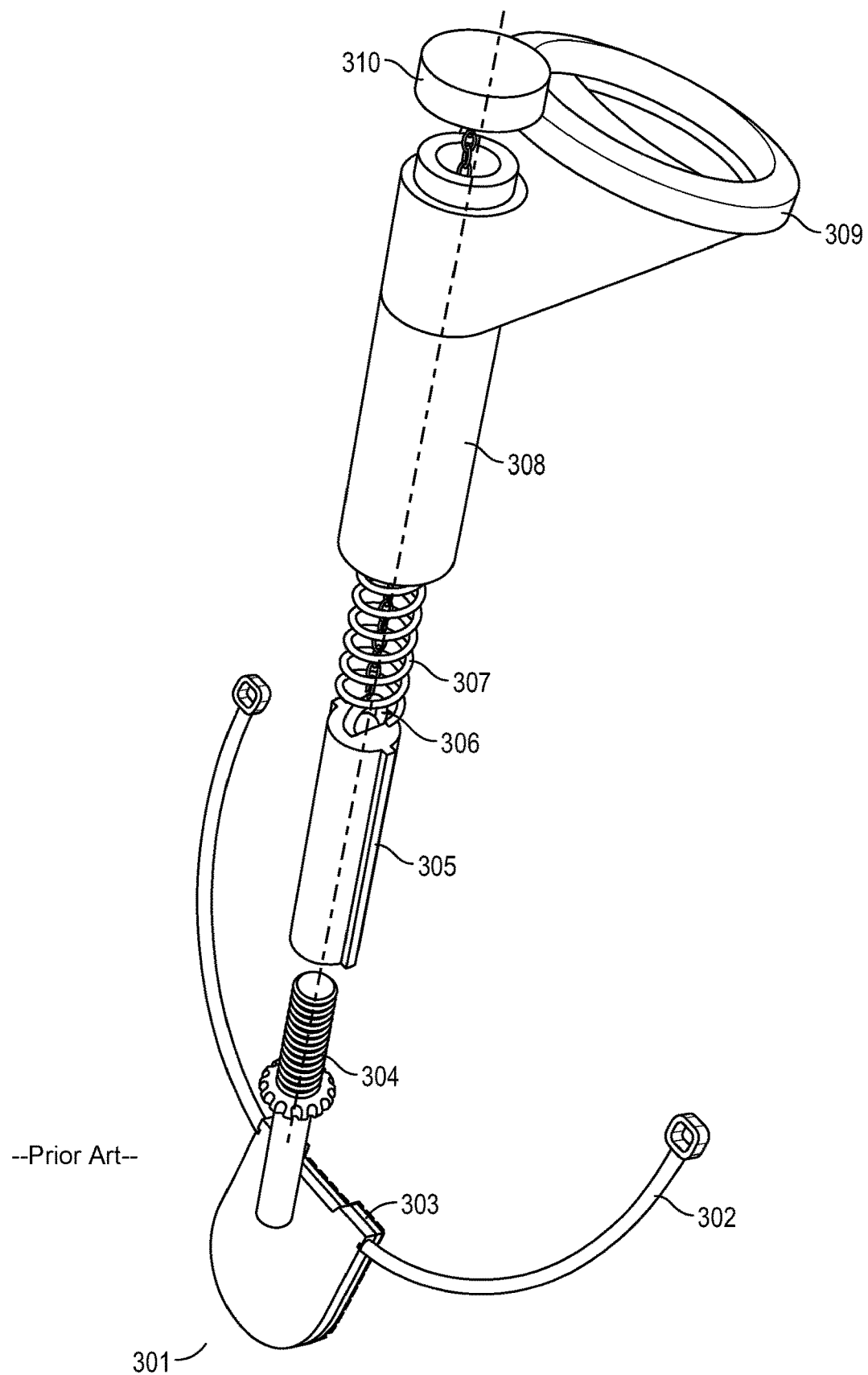
FIG. 4 is a pictorial illustration of an exploded view of the prior invention, similar to FIG. 2, but from a top-side favored perspective viewpoint.

Reference is now made to FIGS. 3 and 4 which are meant to communicate additional views of the device, with emphasis on the construction of the overall device and the relation between the various components.

FIG. 3 is a perspective and partially exploded view of an embodiment of the prior invention, from a low angle, indicating the major components and how they attach, nest, or lock together.

FIG. 4 is another perspective and partially exploded view of an embodiment of the prior invention from a high angle. Notably, both FIG. 3 and FIG. 4 do not depict all components of the device and leave out the chain which locks and compresses the spring. Additionally, neither FIG. 3 nor FIG. 4 indicates the approximate location and scale of the threading on the cylinders which enables the fine adjustment of the height of the support arm. These features are depicted and disclosed in details in FIG. 5 and FIG. 6.

Figure 5:
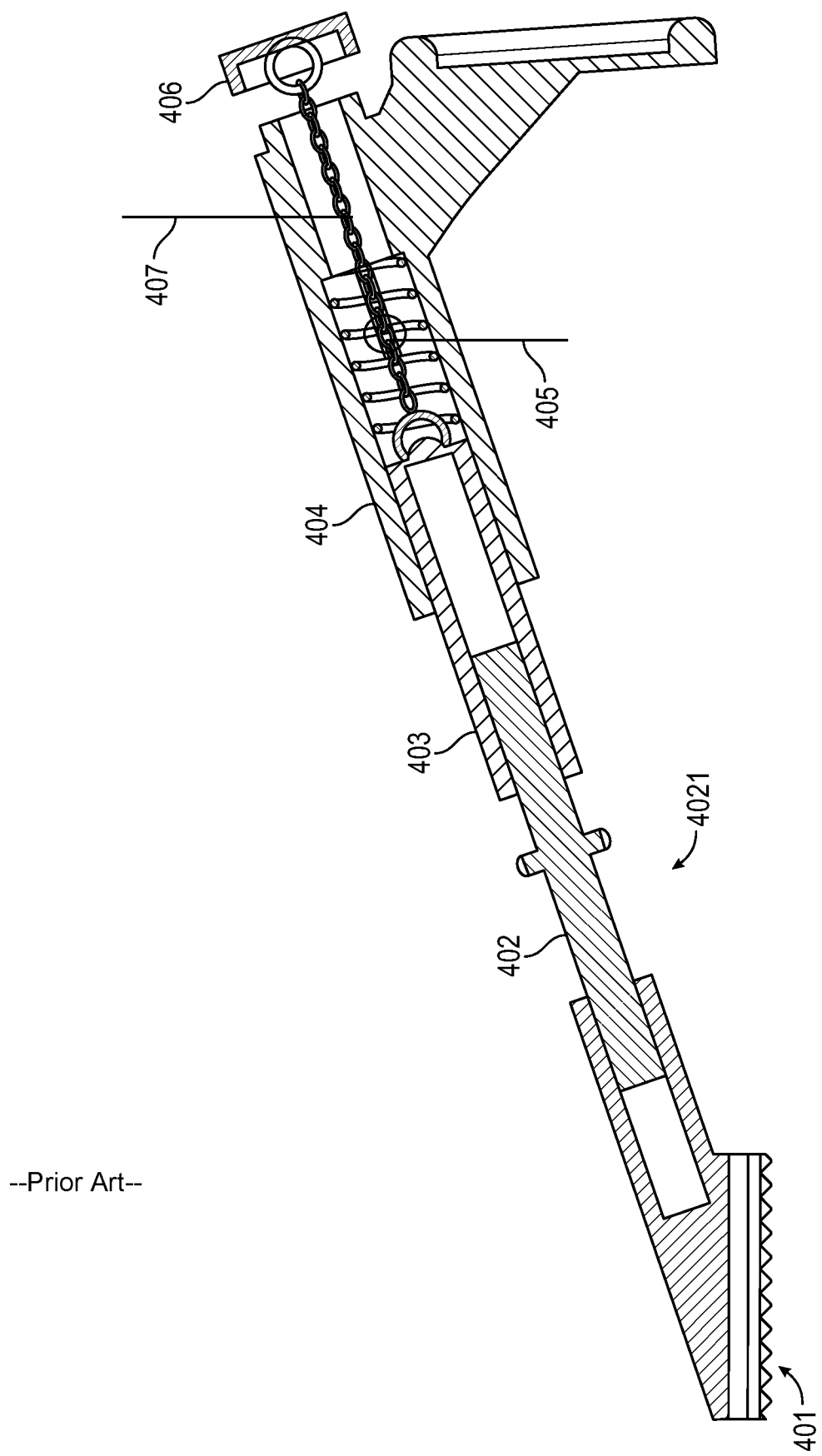
FIG. 5 is a cutaway side-view illustration of the assembled assembly of the support arm mechanism of the prior invention.
Figure 6:
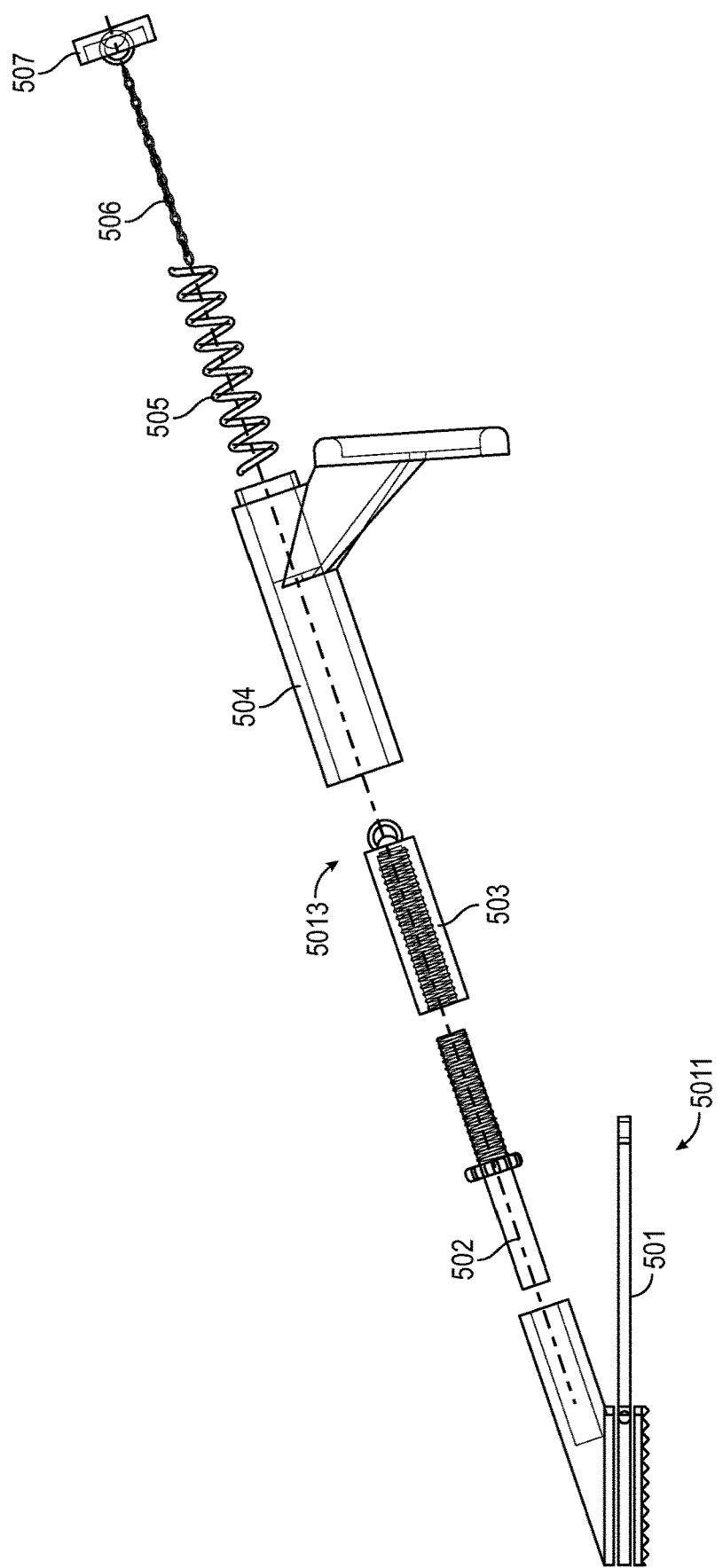
FIG. 6 is a cutaway side-view illustration of an exploded view of the prior invention.

Reference is now made to FIG. 5 wherein a pictorial illustration shows a sectional view of an assembled embodiment of the current invention. FIG. 6 shows the dependencies and how the various cylindrical components nest and connect to one another.

When in use, the main base 401 of the embodiment rests against the user's sternum. A cylinder 402 is inserted into base 401 hollow. Near the other end of this cylinder 402, it further comprises an extruded radial surface 4021 which serves to ensure that the base 401 and this cylinder 402 are attached at a static height. This radial surface 4021 serves to act as a rotational dial, which a practitioner or user turns in order to raise or lower the support arm. This is accomplished by the previously described threading, cylinder 402 having male threading from the dial to the top of the cylinder which then pairs with the female threading on the lower end of cylinder 403 which receives cylinder 402.

Cylinder 403 is then inserted into component 404 which comprises a hollow cylinder and a chin rest component molded to the outer side of the hollow cylinder. As seen in FIG. 5, the spring 405 rests on the top of the cylinder 403 and is then contained by component 404, with component 404 acting as the sides and top. Component 404 also acts a stopper of the spring 405. To achieve this effect, the far end of component 404 has a narrower diameter that is smaller than that of sprint 405 and component 404 near end. As such, vertical pressure may be applied to the chin rest component, the far end of component 404, in turn, presses down on the spring 405 and compresses it, raising and lowering component 404 with it.

As can be seen, one end of a chain 407 connects to a ring that is attached to the end of cylinder 403. The other end of the chain 407 threads up and through the open top of component 404 and is attached to an endcap 406. This endcap 406 is what allows a practitioner or user to then turn and mechanically lock in the height of this portion of the device, holding the spring in place.

In FIG. 6, an exploded sectional view of an embodiment of the prior invention is depicted. This embodiment comprises a base 501 that further comprises a belt 5011 that, when in use, wraps the user's chest, locks, and attaches the device to the user's body. The embodiment further comprises a cylinder 502 that has a radial ring attached near the far end of the cylinder 502. The cylinder 502's far end is male threaded, and screwed into a hollow cylinder 503 that is female threaded. This method of attachment enables the height adjustment feature of the device. The cylinder 503 further comprises a ring 5031 that is attached to its far end. The embodiment further comprises a component 504 that in turn comprises a hollow cylinder and a chin rest component molded to the outer side of the cylinder. The cylinder 503 disposes within the hollow cylinder of the component 504. The embodiment further comprises a spring 505 is also disposed within the hollow cylinder of the component 504. The 404 hollow cylinder has open ends, and the far end opening has a smaller diameter than the diameter of the spring 505. Thus, the spring 505 is contained inside the 404 hollow cylinder, and pushes against the 404 hollow cylinder from the inside. To restrain the spring 505 and prevent the spring 505 from pushing the component 404 away from the assembly, the embodiment further comprises a chain 506 and end cap 507. One end of the chain 506 is attached to the ring 5031, and the other end is attached to the cavity of the end cap 507. The end cap 507 covers the far end opening of the component 504, and the chain 506 and the end cap restrain the component 404, and prevent it from being pushed away by the spring 505. The length or height of this embodiment is adjustable by turning the radial ring on cylinder 502 or the end cap 507, and, consequently, pushing up or pulling down the cylinder 503, and thus extending or contracting the device.

Figure 7:
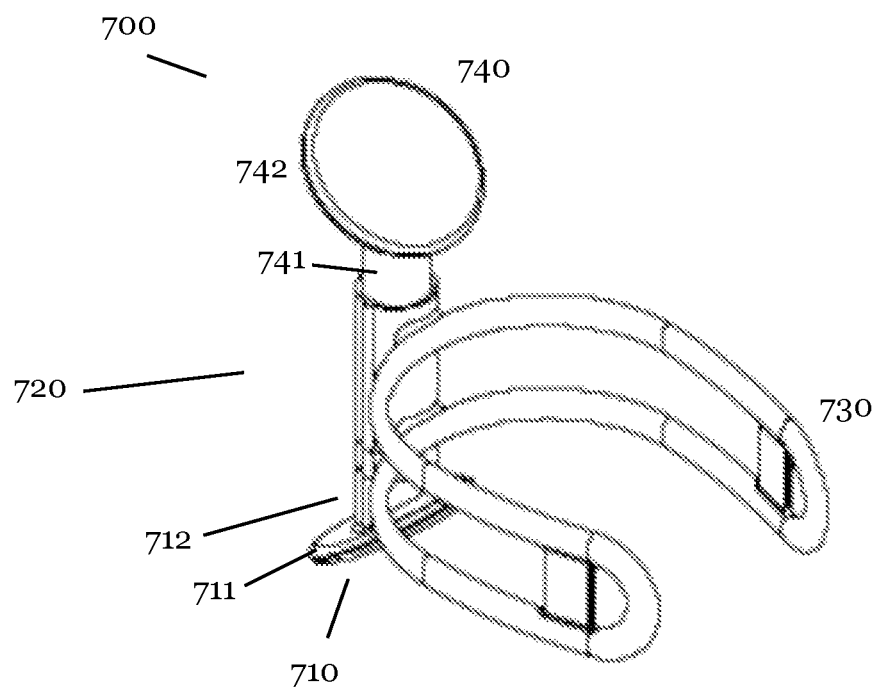
FIG. 7 is a perspective view of now improved embodiment of the current invention.

FIG. 7 illustrates another fully assembled embodiment 700 of prior invention. This embodiment 700 comprises a base component 710 that, when in use, rests on the user/patient's sternum and supports the weight pushing down on the device. This base component 710 further comprises a disc 711 and a hollow cylindrical tube 712 attached to the disc 711 at an angle. The embodiment 700 further comprises a cylindrical body 720, when assembled, sitting in the hollow cylindrical tube 712. The embodiment 700 further comprises a horseshoe shaped elastic band 730 that is attached to and around the midlength of the cylindrical body 720, and extends and wraps around the user/patient's sides. When in place, its elasticity causes the band to hug the user's body tightly, and, thus, keeps this embodiment on the user's sternum. The upper end of the cylindrical body 720 is hollow to receive the chin rest 740, which comprises a cylindrical tube 741 attached underneath a disc 742. It is contemplated that disc 742 has an indentation for the user's chin.

Figure 8:
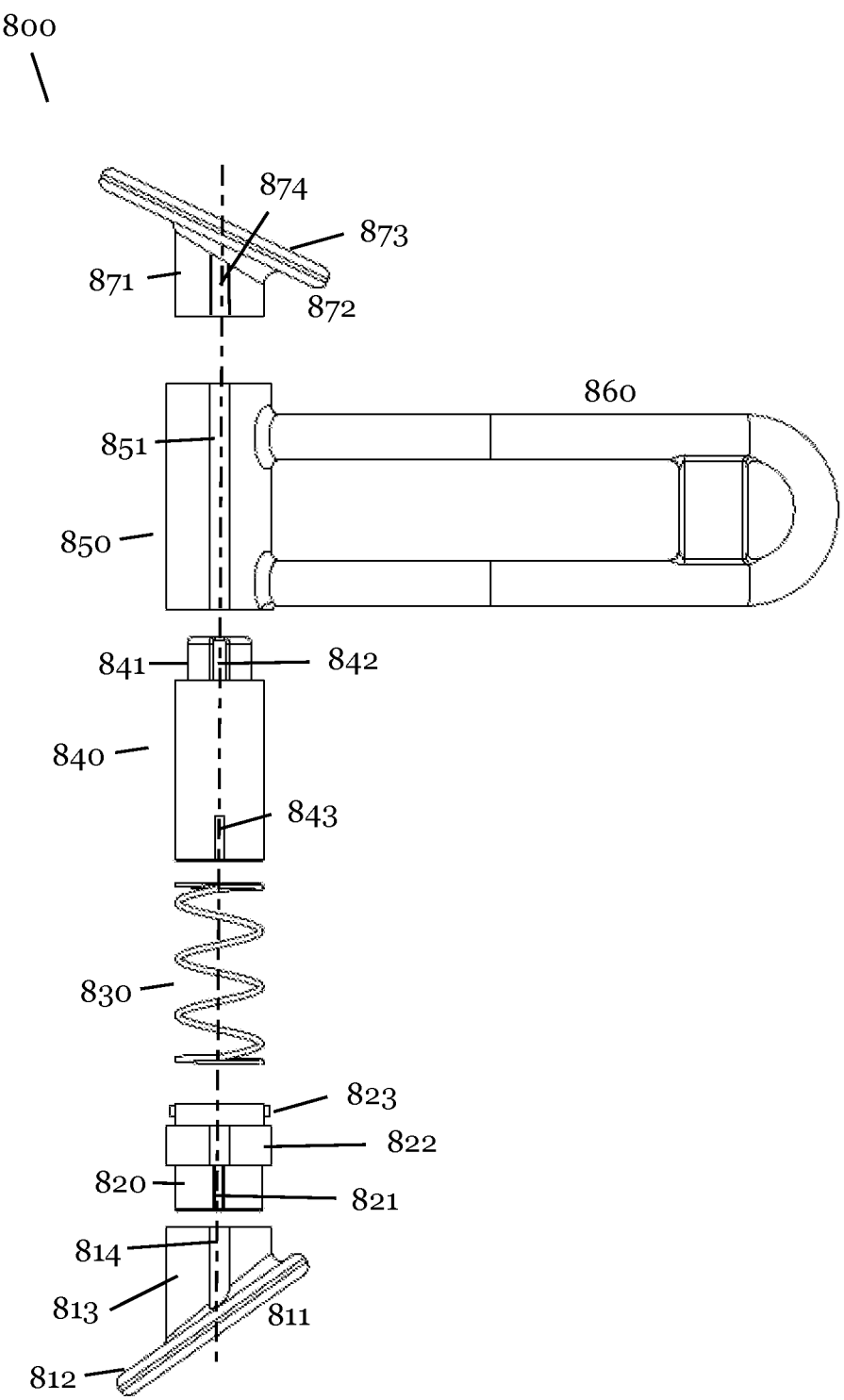
FIG. 8 is an exploded side view of another embodiment of the now improved current invention.

FIG. 8 illustrates an exploded side view of another embodiment 800 of now the improved invention, where the base component comprises a disc that further comprises a top and bottom halves, 812 and 811. This exploded view shows the various individually components, their approximate location to other components in the final assembly, and a suggestion of how those components are constructed and operative in accordance with an embodiment of the present invention. The bottom half 811 is, in this embodiment, a pad that is attached to and removable from the top half 812 by a variety of methods of attachment, such as Velcro patch. The pad 811 is made of elastic materials, such as memory foam, to provides comfort to the user. The top half 812 is attached to a hollow tube 813 at its slanted end. For this slanted angle, the base disc is disposed slanted and, thus, could rest on the down-slope of the user's sternum. When said base component sits on the sternum, it prods the whole device up and provides support for the chin. Said hollow tube 813 further comprises two vertical grooves 814 on the inside walls of the tube 813, and opposite each other.

The embodiment 800 further comprises a cylindrical component 820 that has a smaller diameter than that of tube 813 so that the component 820 can be inserted therein. On the outer wall of the cylindrical component 820 there disposed two vertical ridges 821 opposite each other and made to mate with the grooves 814. The component 820 further comprises a sleeve 822 attached to the outside wall. The sleeve 822 has a larger diameter which is at least equal to that of cylinder 813. The sleeve 822 is disposed about the middle of the component 820. The component 820 further comprises two tabs 823 disposed on the outer wall about the edge thereof, and opposite each other. There is a gap between these tabs 823 and the sleeve 822. When assembled, the lower half of this cylindrical component 820 is inserted into tube 813 of the base component, and held there. The upper half above the sleeve 822 extends up to support other components of the device.

The embodiment 800 further comprises a spring coil 830 that has a diameter larger than that of said component 820, but smaller than that of said sleeve 822. When assembled, the first ring at the one end of the spring coil 830 is disposed in the gap between the sleeve 822 and the tabs 823, and the sleeve and tabs hold the spring coil there in vertical position. The other end of the spring coil extends up to support other components.

The embodiment 800 further comprises a cylindrical component 840 that comprises a lower half that has a diameter equal to that of the spring coil 830, such that the cylindrical component 840 cannot be deposited inside the spring coil. The component 840 further comprises an upper half 841 that has a smaller diameter. This upper half 841 further comprises two vertical ridges 842 disposed on its outer wall and opposite each other. The component 840's lower half further comprises two vertical ridges 843 disposed on the outer wall thereof and opposite each other. When assembled, the lower half of the component 840 sits on the one end of the spring coil 830, and the upper half extends up to support other components.

The embodiment 800 further comprises a hollow tube 850 that has a diameter equal to that of the sleeve 822. The tube 850 further comprises two vertical grooves 851, opposite each other, on the inner wall thereof. When assembled, the grooves 851 engages with the ridges 843 such that the ridges 843 slide and sit in the grooves. This way, the ridges 843 constrains the tube 850 from rotating relative to components 840, and the device. The sleeve catches the tube 850 and constrains it from moving down further.

In one embodiment, the tube 850 further comprises two vertical grooves 851, having limited clearance at their one end, opposite each other, on the inner wall thereof. When assembled, the grooves 851 engages with the ridges 843 such that the ridges 843 slide and sit in the grooves. This way, the ridges 843 constrains the tube 850 from rotating relative to components 840, and constrains the components 840 from sliding through and out of the hollow tube 850.

The embodiment 800 further comprises a horseshoe shaped elastic band 860 that is attached to the outer wall of the tube 850. The elasticity of the band 860 allows the gap between the band's left and right parts to open wider so the user could put the band, and thus the device, on around the user's body. When the left and right parts return to their rest positions, the band hugs the user's body tightly.

The embodiment 800 further comprises a chin rest that in turn comprises a hollow tube 871, a disc 872, and a pad 873. The disc 872 is attached to the slanted end of the tube 871. For the slanted angle, the disc is disposed slanted toward the user, and allows the user's chin rests comfortably on it. The pad 873 is attached to and removable from the disc 872. It is contemplated that the pad 873 further provides comfort to the user with its conforming material, such as memory foam, and/or an indentation for the chin. The tube 871 has a diameter larger than the upper half 841 but smaller than the tube 850. Furthermore, the tube 871 comprises two vertical grooves 874 on the inner wall, opposite each other. When assembled, the tube 871 sits on the component 840 whose upper half 841 inserted in it. The vertical grooves 874 engage with the ridges 842 on the upper half 841. This way, the tube 871, and the chin rest, is constrained from rotating relative to the component 840, and the device in general.

Figure 9:
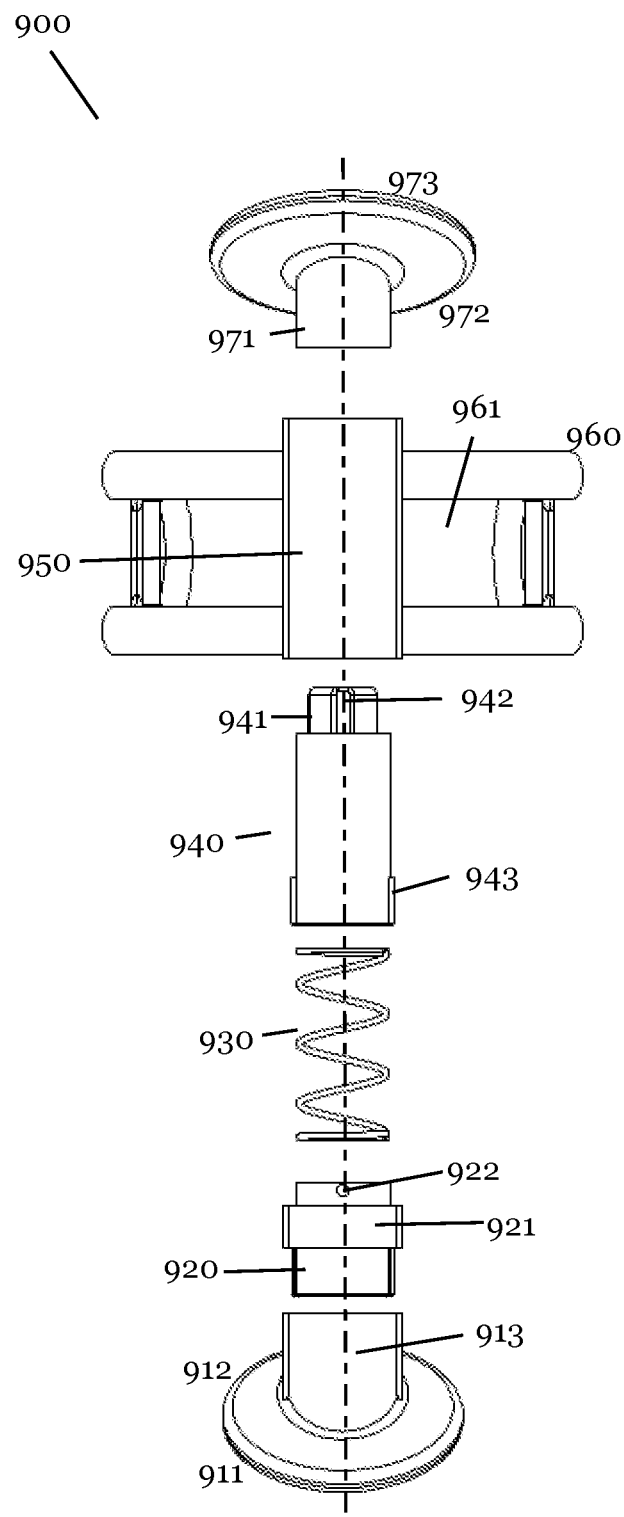
FIG. 9 is an exploded back view of another embodiment of the now improved current invention.

FIG. 9 illustrates an exploded back view of an embodiment 900 of the current invention. This exploded view shows the various individually components, their approximate location to other components in the final assembly, and a suggestion of how those components are constructed and operative in accordance with an embodiment of the present invention. Similar to the embodiment 800, the embodiment 900 comprises a base component that in turn comprises a base disc that further comprises a bottom and top halves, 911 and 912. The bottom half 911 is, in this embodiment, a pad that is attached to and removable from the top half 912 by a variety of methods of attachment, such as Velcro patch. The top half 912 is attached to a hollow tube 913 at its slanted end. Thus, the base disc is disposed slanted and, thus, could rest on the down-slope of the user's sternum.

The embodiment 900 further comprises a cylindrical component 920 that has a smaller diameter than that of tube 913 so that the component 920 can be inserted therein. The component 920 further comprises a sleeve 921 attached to the outside wall. The sleeve 921 has a larger diameter which is at least equal to that of cylinder 913. The sleeve 921 is disposed about the middle of the component 920. The cylindrical component 920 further comprises two tabs 922 disposed on the outer wall about the one edge thereof, and opposite each other. There is a gap between these tabs 922 and the sleeve 921. When assembled, the lower half of this cylindrical component 920 is inserted into tube 913 of the base component, and held there. The upper half above the sleeve 921 extends up to support other components of the device.

The embodiment 900 further comprises a spring coil 930 that has a diameter larger than that of said component 920, but smaller than that of said sleeve 921. When assembled, the first ring at the one end of the spring coil 930 is disposed in the gap between the sleeve 921 and the tabs 922, and the sleeve and tabs hold the spring coil there in vertical position. The other end of the spring coil extends up to support other components.

The embodiment 900 further comprises a cylindrical component 940 that comprises a lower half that has a diameter equal to that of the spring coil 930, such that the cylindrical component 940 cannot be deposited inside the spring coil. The lower half further comprises two vertical ridges 943 disposed on the outer wall thereof and opposite each other. The component 940 further comprises an upper half 941 that has a smaller diameter. This upper half 941 further comprises two vertical ridges 942 disposed on its outer wall and opposite each other. When assembled, the lower half of the component 940 sits on the one end of the spring coil 930, and the upper half 941 extends up to support other components.

The embodiment 900 further comprises a hollow tube 850 that has a diameter equal to that of the sleeve 921. When assembled, the sleeve 921 catches the tube 950 and constrains it from moving down further.

The embodiment 900 further comprises a horseshoe shaped elastic band 960 that is attached to the outer wall of the tube 950 facing the user's body. The elasticity of the band 960 allows the gap 961 between the band's left and right parts to open wider so the user could put the band, and thus the device, on around the user's body. When the left and right parts return to their rest positions, the band hugs the user's body tightly.

The embodiment 900 further comprises a chin rest that in turn comprises a hollow tube 971, a disc 972, and a pad 973. The disc 972 is attached to the slanted end of the tube 971. Thus, the disc 972 is disposed slanted toward the user, and allows the user's chin rests comfortably on it. The pad 973 is attached to and removable from the disc 972. It is contemplated that the pad 973 further provides comfort to the user with its conforming material, such as memory foam, and/or an indentation for the chin. The tube 971 has a diameter larger than the upper half 941 but smaller than the tube 950. When assembled, the tube 971 sits on the component 940 whose upper half 941 inserted in it.

Figure 10:
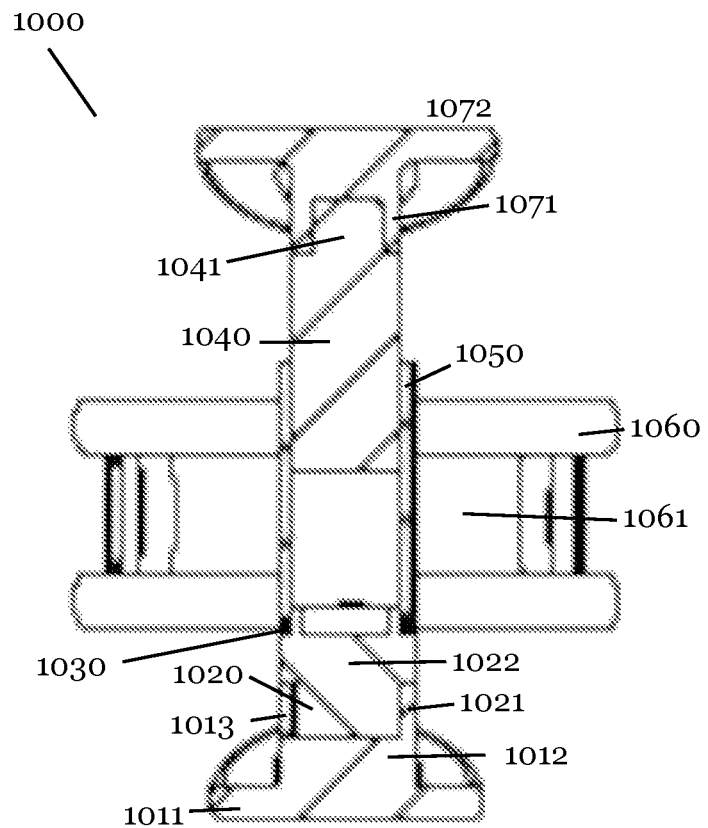
FIG. 10 is a sectional back view of another embodiment of the now improved current invention.

FIG. 10 illustrates a sectional back view of an embodiment 1000 of the current invention, and indicates the major components and how they attach, nest, or lock together when the device is fully assembled. Similar to the embodiments 800 and 900, the embodiment 1000 comprises a base component that in turn comprises a disc 1011 and a hollow tube 1012. The disc 1011 is attached to a hollow tube 1012. Said hollow tube 1012 further comprises two vertical grooves 1013 on the inside walls of the tube, and opposite each other.

The embodiment 1000 further comprises a cylindrical component 1020 that has a smaller diameter than that of tube 1012 so that the component 1020 can be inserted therein. On the outer wall of the cylindrical component 1020 there disposed two vertical ridges 1021 opposite each other and made to mate with the grooves 1013. The component 1020 further comprises a sleeve 1022 attached to the outside wall. The sleeve 822 has a larger diameter which is at least equal to that of cylinder 1012. The sleeve 1022 is disposed about the middle of the component 1020. When assembled, the lower half of this cylindrical component 1020 is inserted into tube 1012 of the base component, and held there. The upper half above the sleeve 1022 extends up to support other components of the device.

The embodiment 1000 further comprises a spring coil 1030, partially hidden and only its first ring is shown in FIG. 10, that has a diameter larger than that of said component 1020, but equal to that of said sleeve 1022.

The embodiment 1000 further comprises a cylindrical component 1040 that comprises a lower half that has a diameter equal to that of the spring coil 1030, such that the cylindrical component 1040 cannot be deposited inside the spring coil. The component 1040 further comprises an upper half 1041 that has a smaller diameter. When assembled, the lower half of the component 1040 sits on the one end of the spring coil 1030, and the upper half 1041 extends up to support other components.

The embodiment 1000 further comprises a hollow tube 1050 that has a diameter equal to that of the sleeve 1022.

When assembled, the sleeve 1022 catches the tube 1050 and constrains it from moving down further.

The embodiment 1000 further comprises a horseshoe shaped elastic band 1060 that is attached to the outer wall of the tube 1050 facing the user's body. The elasticity of the band 1060 allows the gap 1061 between the band's left and right parts to open wider so the user could put the band, and thus the device, on around the user's body. When the left and right parts return to their rest positions, the band hugs the user's body tightly.

The embodiment 1000 further comprises a chin rest that in turn comprises a hollow tube 1071 and a disc 1072. The disc 1072 is attached to the slanted end of the tube 1071. Thus, the disc is disposed slanted, and allows the user's chin rests comfortably on it. The tube 1071 has a diameter larger than the upper half 1041. When assembled, the tube 1071 sits on the component 1040 whose upper half 1041 inserted in it.

Figure 11:
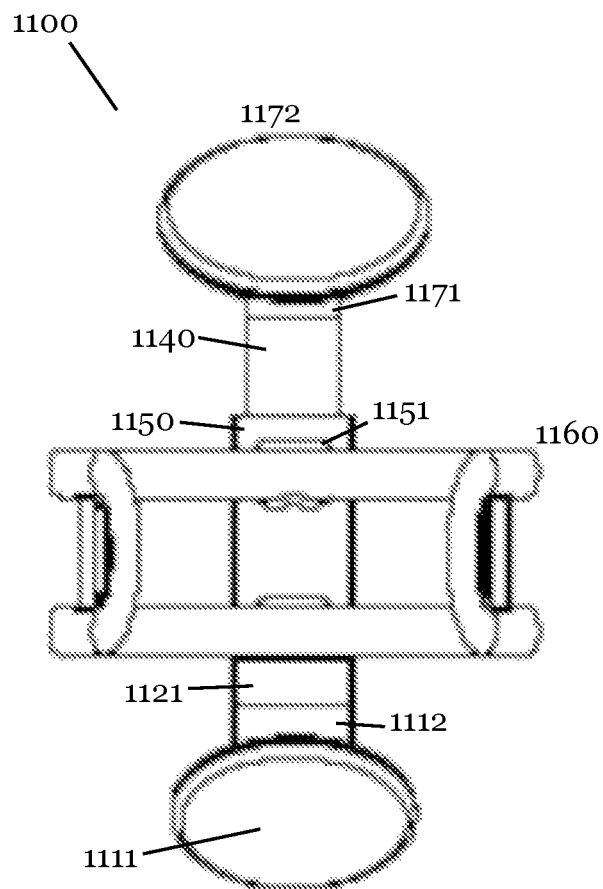
FIG. 11 is a front view of another embodiment of the now improved current invention.

FIG. 11 illustrates a front view of a fully assembled embodiment 1100 of the current invention. Similar to the embodiments 800, 900, and 1000, the embodiment 1100 comprises a base component that in turn comprises a disc 1111 and a hollow tube 1112, which are attached to each other. The embodiment 1100 further comprises a cylindrical component that comprises a sleeve 1121 attached to its outside wall. The sleeve 1121 has a larger diameter which is at least equal to that of the cylinder 1112. In FIG. 11, only the sleeve 1121 of the cylindrical component is shown. The sleeve 1121 is disposed about the middle of the cylindrical component. When assembled, the lower half of this cylindrical component is inserted into tube 1112 of the base component, and held there. The upper half above the sleeve 1121 extends up to support other components of the device.

The embodiment 1100 further comprises a hollow tube 1150 that has a diameter equal to that of the sleeve 1121. When assembled, the sleeve 1021 catches the tube 1150 and constrains it from moving down further. The embodiment 1100 further comprises a horseshoe shaped elastic band 1160 that is attached to the outer wall of the tube 1150 facing the user's body. In this embodiment, the tube 1150 further comprises a pair of brackets 1151 attached to it outer wall by a variety of attachment methods. The brackets 1151 then receive the upper and lower parts of said elastic band 1160.

The embodiment 1100 further comprises a cylindrical component 1140 that comprises a lower half that is hidden from view inside the tube 1150 in this view. The lower half of component 1140 sits on the cylindrical component which comprises the sleeve 1121. The component 1140 further comprises an upper half that has a smaller diameter, and not shown in this view. When assembled, the upper half extends up to support other components.

The embodiment 1100 further comprises a chin rest that in turn comprises a hollow tube 1171 and a disc 1172. The disc 1072 is attached to the slanted end of the tube 1171. Thus, the disc is disposed slanted, and allows the user's chin rests comfortably on it. The tube 1171 has a diameter larger than the upper half of the cylindrical component 1140. When assembled, the tube 1171 sits on the component 1140 whose upper half inserted in it.

The invention claimed is:

1. A head and/or neck support device comprising:
a) a base component comprising a disc that further comprises a top portion and a bottom portion; wherein said bottom portion is a bottom pad that is attached to and removable from said top portion; wherein said top portion is attached to a hollow tube at its slanted end; wherein said base disc is disposed on to said slanted end and thereby configured to rest on a downward slope of a user's sternum; wherein when said base component is configured to sit on said sternum, allowing said head and/or neck support device to provide support for the chin of said user; wherein said hollow tube further comprises two vertical grooves on the inside walls of said tube and opposite to each other;
b) a first cylindrical component that has a smaller diameter than that of said hollow tube so that said first cylindrical component can be inserted therein; wherein on an outer wall of said first cylindrical component are disposed two vertical ridges opposite each other and made to mate with said vertical grooves; wherein a sleeve attached to said outside wall wherein said sleeve has a larger diameter which is at least equal to that of said first cylinder component; wherein said sleeve is disposed about the middle of said first cylindrical component; wherein two tabs disposed on said outer wall about the edge thereof, and opposite each other thereby allowing a gap between said tabs and said sleeve;
wherein said lower half of said first cylindrical component is inserted into said hollow tube of said base component while the portion above said sleeve extends up to support other components of said device;
c) a spring coil that has a diameter larger than that of said first cylindrical component, but smaller than that of said sleeve and is disposed in a gap between said first cylindrical component and a second cylindrical component wherein said tabs holds said first cylindrical component securely with a second hollow tube;
d) said second cylindrical component comprising a lower portion that has a diameter equal to that of said spring coil, such that said second cylindrical component cannot be deposited inside said spring coil;
wherein an upper portion has a smaller diameter than said lower portion wherein said upper portion further comprises two second vertical ridges disposed on its outer wall and opposite each other;
e) said second hollow tube further comprises second two vertical grooves, opposite each other and on the inner wall thereof; wherein said second grooves engages with said second ridges of said upper portion of said second cylindrical component such that said second ridges slide and sit in on said second grooves wherein said second ridges constrains said second tube from rotating relative to said second cylindrical components and constrains said second cylindrical component tube from sliding out and through said second hollow tube;
f) a horseshoe shaped elastic band attached to the outer wall of said second hollow tube wherein said elasticity of the band allows a gap between the band's left and right parts to open wider so said user could put the band on and around said user's neck;
g) a chin rest comprises a third hollow tube, a disc, and a top pad wherein said disc is attached to said slanted end of said third tube wherein said top disc is disposed slanted toward the user, and allows the user's chin rests comfortably on it.

2. The device of claim 1 wherein said bottom pad that is attached to and removable from said top portion via a VELCRO patch.

3. The device of claim 1 wherein said bottom pad is made of elastic materials.

4. The device of claim 3 wherein said elastic materials is a memory foam.

5. The device of claim 1 wherein said top pad is attached to and removable from said top disc.

6. The device of claim 1, wherein said top pad is further configured to provide comfort to the user with its conforming material.

\* \* \* \* \*